United States Patent [19]

Nagai et al.

[11] Patent Number: 5,091,557

[45] Date of Patent: Feb. 25, 1992

[54] AMINO ACID DERIVATIVE HAVING LIQUID CRYSTAL PROPERTY AND PROCESS FOR PRODUCTION OF THE SAME

[75] Inventors: Kimie Nagai; Schuichi Naijoh; Ayako Kurotaki; Koro Shirane; Chozo Inoue, all of Tokyo, Japan

[73] Assignee: Showa Denko K.K., Tokyo, Japan

[21] Appl. No.: 701,906

[22] Filed: May 17, 1991

Related U.S. Application Data

[62] Division of Ser. No. 501,220, Mar. 29, 1990.

[30] Foreign Application Priority Data

Mar. 31, 1989 [JP] Japan .................................. 1-82760
Sep. 22, 1989 [JP] Japan .................................. 1-245199

[51] Int. Cl.$^5$ .......................................... C07C 279/00
[52] U.S. Cl. ...................................................... 560/39
[58] Field of Search .......................................... 560/39

[56] References Cited

U.S. PATENT DOCUMENTS

| | | | |
|---|---|---|---|
| 4,764,619 | 8/1988 | Guajima et al. | 560/39 |
| 4,824,217 | 4/1989 | Chou et al. | 560/39 |
| 4,941,992 | 7/1990 | Jackson et al. | 560/39 |

Primary Examiner—Bruce Gray
Attorney, Agent, or Firm—Sughrue, Mion, Zinn, Macpeak & Seaas

[57] ABSTRACT

A novel amino acid derivative is disclosed, which is produced using a relatively inexpensive amino acid as a starting material for an optically active moiety and shows a chiral nematic phase or a chiral smectic phase over a wide temperature range around room temperature. A process for producing the amino acid derivative is also disclosed.

2 Claims, 2 Drawing Sheets

AMINO ACID DERIVATIVE HAVING LIQUID CRYSTAL PROPERTY AND PROCESS FOR PRODUCTION OF THE SAME

This is a divisional of application Ser. No. 07/501,220 filed Mar. 29, 1990.

FIELD OF THE INVENTION

This invention relates to a novel amino acid derivative having a liquid crystal property and a process for producing the compound.

BACKGROUND OF THE INVENTION

Known liquid crystal compounds involve cholesteric liquid crystal compounds and nematic ones. Cholesteric liquid crystals have various optical properties based on a helical structure, for example, optical rotatory power, selective scattering of light, circular dichroism. These phenomena have been widely applied to a number of purposes wherein a color change of cholesteric liquid crystals caused by the application of voltage, a change in temperature or the adsorption of a gas is utilized. As particular examples of the application of cholesteric liquid crystals, there may be mentioned liquid crystal thermometers, pressure sensors, infrared light meters and microwave meter detectors. Many cholesterol compounds show cholesteric liquid crystal property. In addition, cholesteric liquid crystals can be obtained by dissolving an optically active substance having an optical rotatory power in nematic liquid crystals or by introducing an asymmetric carbon atom into a molecular structure of nematic liquid crystals. These liquid crystals, which are called chiral nematic liquid crystals, would not essentially differ from cholesteric liquid crystals of cholesterol compounds. However the former ones are superior to the latter ones in chemical and optical stability and thus have been employed instead of cholesterol liquid crystals.

Examples of such chiral nematic liquid crystals include N-(4-ethoxybenzylidene)-4-2-methylbutyl)aniline and 4-(2-methylbutyl)benzoic acid-4'-n-hexyloxyphenyl ester.

A substance to be used as chiral nematic liquid crystals should be highly stable to moisture, air, light and heat and sustain a cholesteric phase over a wide range of temperature at which a display element is to be used in general.

Although compounds or compositions mainly employed in liquid crystal display devices at present comprise these nematic liquid crystals, they have a serious disadvantage, namely, a low response speed of a several millisecond order. Thus it is considered that the enlargement of these display devices might be restricted thereby.

In order to improve this disadvantage of known liquid crystal display devices, N. A. Clark and S. T. Largerwall proposed to use liquid crystals having a bistability, as described in JP-A-56-107216. (The term "JP-A" herein used means an "unexamined published Japanese patent application".) These liquid crystals having a bistability are called ferroelectric liquid crystals and attract public attention since they can give high speed response and memory properties. Recently, it has been frequently attempted to put these ferroelectric liquid crystals into practical use. Thus it has been urgently required to develop practically available ferroelectric liquid crystal materials.

Generally speaking, the ferroelectricity is actualized with a compound having an optically active moiety in a smectic phase where the long axis of the molecule shows an orientation tilting against the normal direction of the layer made of the compound. A chiral smectic phase (hereafter referred to as $S_c^*$) is particularly advantageous from a practical viewpoint since the driving voltage thereof is relatively low.

Thus ferroelectric liquid crystals exhibit an extremely high response due to spontaneous polarization, can express a bistable state of high memory properties, has an excellent viewing angle, and are suitable for a display material of a large capacity and a large picture.

A known example of such ferroelectric liquid crystal compounds is (S)-2-methylbutyl 4-(4-decyloxybenzylideneamino)cinnomate (hereafter referred to as DOBAMBC) synthesized by R. B. Meyer et al. as described in *J. Physique*, 36 L-69 (1975).

This DOBAMBC contains a Schiff base in its structure, which causes a problem in chemical stability. Therefore there has been attempted to find out ferroelectric liquid crystal compounds which are physically and chemically stable. Now the main current of these studies goes toward esters such as (S)-2-methylbutyl 4-(4-n-alkoxybenzoyloxy)benzoate. However, these esters would show either no $S_c^*$ phase or an $S_c^*$ phase, if any, within a considerably narrow temperature range. Furthermore, they are monotropic liquid crystals whose phase system achieved by heating the liquid crystals to a certain temperature differs from that achieved by cooling the same to the same temperature. Accordingly, there are only a few compounds which are practically applicable, as described in *Liquid Crystals and Ordered Fluids*, 4 (1984).

Particular examples of sources for providing optically active moieties of known ferroelectric liquid crystal compounds involve optically active alcohols such as 2-methylbutanol and 3-methylpentanol. However these alcohols are expensive, which brings about a problem in production cost. JP-A-62-89648 proposes to use an amino acid, which can be more easily obtained at a lower cost, as an optically active material. According to this report, however, the product thus obtained would show only a smectic A phase at a high temperature and therefore is not practical.

SUMMARY OF THE INVENTION

An object of the present invention is to provide a novel compound, which is obtained using an inexpensive and easily available amino acid as a starting material for providing an optically active moiety and can show a chiral nematic phase or a chiral smectic phase over a wide temperature range, as well as a process for producing of the same.

The compound provided by the present invention is a novel amino acid derivative represented by formula (I):

wherein R represents a straight chain alkyl group having 6 to 16 carbon atoms; A represents X represents a straight chain alkyl group having 1 to 14 carbon atoms; Y represents —CH₃, —CH₂CH(CH₃)₂, —CH(CH₃)₂, —CH(CH₃)CH₂CH₃ or Z represents —CN, —CH₃ or a hydrogen atom; and C* represents an asymmetric carbon atom.

DETAILED DESCRIPTION OF THE INVENTION

The structure of the amino acid derivative of the present invention may be divided into an amino acid moiety, which is the source of its optical activity, of the following formula:

and a cinnamic acid derivative moiety, which is the core, of the following formula:

These two moieties are bound to each other via a peptide bond.

In the amino acid moiety, a hydrogen atom, Y and —COOX are bound to the asymmetric carbon C* and the amine moiety forms a peptide bond. In the above formula, X represents a straight chain alkyl group having 1 to 14, preferably 1 to 3, carbon atoms. When X has 15 or more carbon atoms, a starting material therefor is not readily available and, furthermore, the synthesis of the product is difficult.

In the above formula, Y represents a group selected from among —CH₃, —CH₂CH(CH₃)₂, —CH(CH₃)₂, —CH(CH₃)CH₂CH₃ and with —CH(CH₃)₂ and —CH(CH₃)CH₂CH₃ being preferred. Any amino acid may be used as a starting material for providing the amino acid moiety, so long as it is optically active. Examples thereof include L-alanine, leucine, L-valine, isoleucine and phenylalanine. It is particularly preferable to use L-valine or isoleucine therefor since these amino acids can give a ferroelectric liquid crystal property. Either D- or L-optically active amino acids may be used therefor.

Next, the cinnamic acid moiety will be described. In this moiety, Z is bound to the unsaturated carbon atom at the α position of cinnamic acid:

with the carboxylic moiety forming a peptide bond together with the amine of the amino acid moiety. Z is —CN, —CH₃ or H, and —CN is particularly preferred for Z since the resulting amino acid derivative show a liquid crystal phase over a wide temperature range. A benzene ring or a biphenyl group is bound at the para-position of the benzene ring of cinnamic acid via an ester bond and R is bound to the para-position of said benzene ring or the 4'-site of said biphenyl group via an ether bond. R represents a straight chain alkyl group having 6 to 16, preferably 7 to 14, carbon atoms. When R has 5 or less carbon atoms, the compound shows a liquid crystal phase over a narrow temperature range. When the carbon atom number in R exceeds 16, on the other hand, it is difficult to obtain such a starting material therefor.

Of the amino acid derivatives represented by formula (I), preferred are those represented by formula (Ia) or (Ib):

(Ia)

wherein R¹ represents a straight chain alkyl group having 6 to 14 carbon atoms, and X, Y, Z and C* are the same as defined in formula (I); and (Ib)

wherein X¹ represents a straight chain alkyl group having 1 to 6 carbon atoms, Y¹ represents —CH₃, —CH$_2$CH(CH$_3$)$_2$, —CH(CH$_3$)$_2$ or —CH(CH$_3$)CH$_2$CH$_3$, and R, Z and C* are the same as defined in formula (I).

The present invention is characterized in that an amino acid is used as the source of the optical activity and that a cinnamic acid derivative, which has been studied by Goodby et al and generally known as a starting material for liquid crystals as described in U.S. Pat. No. 4,613,209 and JP-A-52-89643, is introduced as the core.

When an amino acid is used as the source of optical activity, the peptide bond thus formed shows a large intermolecular force which makes it difficult to exert a liquid crystal property. However the introduction of a cinnamic acid derivative makes it possible to achieve a liquid crystal property over a wide temperature range around room temperature.

It is considered that a compound having a bulky group in the neighborhood of an asymmetric carbon atom would easily exhibit ferroelectricity. It is also observed in the present invention that a compound having a branched substituent for Y in formula (I) bound to the asymmetric carbon atom shows ferroelectricity. Among the compounds of the present invention, ferroelectric ones can be used as ferroelectric liquid crystal devices. Furthermore, the compounds of the present invention showing ferroelectricity as well as those showing no ferroelectricity can be blended with known ferroelectric liquid crystals so as to enlarge the temperature range of ferroelectricity or to improve response properties. Furthermore, they can be blended with optically inactive liquid crystals so as to impart ferroelectricity thereto.

An amino acid derivative of formula (I) wherein A is a benzene ring exhibits a chiral nematic liquid crystal phase. However it is difficult to use this compound alone as a liquid crystal device. Thus it is frequently blended with other liquid crystal compound(s). For example, this compound may be blended with the well-known ferroelectric liquid crystal, DOBAMBC, or with others as described in Kajiyama et al, *Chem. Lett.*, 307 (1988) and W. Kuczynski, S. T. Lagarwall et al, ibid., 146,173 (1987), whereby the resulting mixture exhibits an enlarged temperature range for the Sc* phase and an improved stability.

On the other hand, an amino acid derivative of formula (I), wherein the benzene ring of A is substituted with a more rigid biphenyl group, exhibits a stable smectic liquid crystal phase and ferroelectricity. For example, it shows ferroelectric property over a relatively low temperature range of from 44° to 125 °C. In particular, it shows a useful S$_c$* phase over a temperature range of from 76° to 125° C. (refer to Examples 5 and 9). Thus it is applicable to a constituent of a ferroelectric liquid crystal display device to be used as an electrooptical switching element. This derivative may be used alone as a liquid crystal device. Furthermore, it can be blended with other liquid crystal compound(s).

The compound of the present invention may be produced in the following manner. First, a compound represented by formula (II):

(II)

is reacted with a reaction derivative of a compound represented by formula (III):

(III)

to thereby give as compound represented by formula (IV):

(IV)

Next, the compound of formula (IV) is reacted with a compound represented by formula (V):

R—O—A—COOH. (V)

In the above general formulae (II), (III), (IV) and (V), R, A, X, Y, Z and C* have the same meanings as defined in formula (I).

The process for the production of the compound of the present invention comprises two stages. Namely, the first stage comprises reacting the compound of formula (II) with the compound formula (III) to thereby give the compound of formula (IV) (hereafter referred to as reaction A). On the other hand, the second stage comprises reacting the compound represented by formula (IV) with the compound of formula (V) to thereby give the compound of formula (I) (hereafter referred to as reaction B).

Reaction A

The compound of formula (II) wherein Z is —CN or H is commercially available. The compound of formula (II) wherein Z is —CH$_3$ may be synthesized in a conventional manner, as described in U.S. Pat. Nos. 4,751,018 and 4,748,161, and JP-A-52-89643. For example, it may be obtained by reacting 4-hydroxybenzaldehyde and propionic anhydride with potassium propionate.

The reaction derivative of the compound of formula (III) means a hydrochloride of the compound of formula (III). When X has 2 or less carbon atoms, such a starting material is commercially available. When X has 3 or more carbon atoms, it may be synthesized by a conventional esterification reaction. For example, a commercially available amino acid and an alcohol having a carbon chain of the desired length are treated with thionyl chloride thereby to give the required hydrochloride of an alkyl ester of the amino acid.

The reaction between the acid compound of formula (II) and the amine compound of formula (III) may be effected in a solvent (for example, dichloromethane, carbon tetrachloride, benzene) with the use of N,N'-dicylcohexylcarbodiimde (hereafter referred to DCC) as a binder. This process is referred to DCC method hereafter. The reaction is preferably carried out using 1.0 to 1.4 eq. of the acid compound per 1.0 eq. of the amine compound in the presence of about 50 to 80 eq. of the solvent and 1.0 to 1.4 eq. of DCC. Since the amine compound is used in the form of hydrocholide, 1.0 eq. of a base (e.g., triethylamine) is added in the reaction system. Thus the compound represented by formula (IV) can be obtained.

In a known method, a protective group is added to the hydroxyl group of p-hydroxycinnamic acid of formula (II) and then the obtained compound is esterified by the acid chloride method, followed by eliminating the protective group. In this method, however, the double bond in the cinnamic acid is reduced together with the elimination of the protective group, which makes it impossible to obtain the objective compound. In this invention, the esterification by the above-mentioned DCC method makes it possible to obtain the objective compound via a single-stage reaction at room temperature without requiring any protective group. Furthermore, this process gives a high yield of approximately 80%.

Now, the reaction scheme of the known method as well as that of the DCC method will be given.

(1) Known method

(i) Protection of hydroxyl group

(ii) Esterification by acid chloride method (iii) Elimination of protective group (2) DCC method Reaction B Now the reaction wherein the objective amino acid derivative is formed from the intermediate (IV) produced by reaction A will be described.

The compound of formula V wherein A is a benzene ring may be commercially available. The compound of formula (V) wherein A is a biphenyl group may be obtained by reacting p-hyroxybiphenylcarboxylic acid with an alkyl bromide in an alkali solution. The reaction between the compound of formula (IV) obtained by reaction A and the compound of formula (V) may be effected as follows. First, the compound of formula (V) is converted into an acid chloride by heating under reflux for about 2 to 5 hours together with 5 to 10 eq. of thionyl chloride or oxalyl chloride, per 1 eq. of the compound of formula (V). Next, the obtained product is heated under reflux together with 1 to 1.5 eq. of the compound of formula (IV) and 3 to 6 eq. of pyridine in 5 to 30 ml of a solvent (for example, benzene, toluene, ether). Thus the amino acid derivative of formula (I) can be obtained.

The compound of formula (I) is an optically active amino acid derivative. Furthermore, another optically active amino acid derivative of the same structure, which is obtained by using a racemate as the starting amino acid, is similarly available as a liquid crystal material.

The compound of formula (I) of the present invention is a novel useful amino acid derivative as a liquid crystal compound wherein a cinnamic acid derivative is used as the core while an amino acid is used as the source of optical activity.

When an amino acid is introduced as an optically active group, the peptide bond thus formed has a large intermolecular force and causes an increase in the melting point, which makes the compound unsuitable as a liquid crystal compound. When a cinnamic acid derivative is used as the core, however, it is assumed that the well-balanced carbon chains and ester bonds would accelerate polarization and thus liquid crystal alignment would be easily achieved. Furthermore, it is considered that the introduction of a cyano group (for Z formula (I)) in the neighborhood of the asymmetric carbon atom would inhibit the formation of intermolecular hydrogen bonds so as to exert the same effects as those described above.

When a biphenyl group is introduced into the cinnamic acid derivative moiety, the obtained compound shows stable liquid crystal phases including $S_X^*$ phase (chiral smectic X phase) and $S_C^*$ phase and exhibits ferroelectricity.

These facts indicate that the compound of the present invention is a novel amino acid derivative which is highly applicable to a liquid crystal display element excellent in response and memory properties as in the manner described in U.S. Pat. No. 4,367,924.

The present invention is explained in more detail with reference to, the following Examples, but the invention is not limited thereto. In Examples, Cry, Ch, Iso, $S_A$, $S_C$, $S_C^*$ and $S_X^*$ phases respectively show a crystalline phase, a cholesteric phase, an isotropic phase, a smectic A phase, a smectic C phase, a chiral smectic C phase and a chiral smectic X phase.

Each compound of the present invention was purified by silica gel chromatography and recrystallization from alcohol and hexane. The phase transition temperature as shown below might be somewhat affected by the purity of the product.

In Examples, L-amino acids were used as starting optically active amino acids. However, a product of the same phase transition temperature can be obtained even when the corresponding D-amino acids are used as the starting materials.

EXAMPLE 1

Synthesis of
N-{4-(4'-n-heptyloxybenzoyloxy)-α-cyanocinnamoyl}-
L-alanine ethyl ester (1-1) Synthesis of
N-(4-hydroxy-α-cyanocinnamoyl)-L-alanine ethyl ester 1.04 g (5.5 mmole) of commercially available α-cyano-4-hydroxycinnamic acid was stirred in 10 ml of cold dichloromethane and the temperature of the reaction mixture was adjusted to 0° to 5° C. Then, 1.134 g (5.5 mmole) of DCC was added thereto. Approximately 20 minutes thereafter, 0.768 g (5 mmole) of commercially available L-alanine ethyl ester hydrochloride and 0.7 ml (5 mmole) of triethylamine were added thereto. The mixture thus obtained was stirred at 0° C. for 2 hours and then at room temperature overnight. After distilling off the solvent, the residue was dissolved in 30 ml of ethyl acetate. The insoluble N,N'-dicyclohexyl urea was removed by filtering and the filtrate was successively washed with 30 ml of 10% citric acid, 30 ml of water, 30 ml of 4% sodium hydrogencarbonate and 30 ml of water. The organic phase was dried over magnesium sulfate and evaporated to dryness to thereby give a crude ester product.

The yield was 79%. The unpurified product was subjected to the next treatment as such.

(1-2) Synthesis of
N-{4-(4'-n-heptyloxybenzoyloxy)-α-cyanocinnamoyl}-
L-alanine ethyl ester 0.94 g of heptyloxybenzoic acid, 2.89 ml of thionyl chloride and one drop of DMF (reaction initiator) were heated under reflux for approximately 2 hours to thereby give an acid chloride. After distilling off the thionyl chloride, 1.15 g of the compound synthesized in (1-1), 3.21 ml of pyridine, 5 ml of benzene and one drop of DMF were added to the residue. The obtained mixture was heated under reflux for approximately 5 hours to thereby complete esterification.

After post-treatments, the product was purified by silica gel column chromatography with the use of a mixture of n-hexane and ethyl acetate (5:1) as an eluent. Thus 1.8 g of a crude crystalline compound was obtained. The product was further purified by recrystallization to thereby give the objective compound.

The structure of the obtained product was confirmed by infrared absorption spectrometry, elemental analysis, $^1$H-NMR and mass spectrometry as will be shown below.

Figure 1:
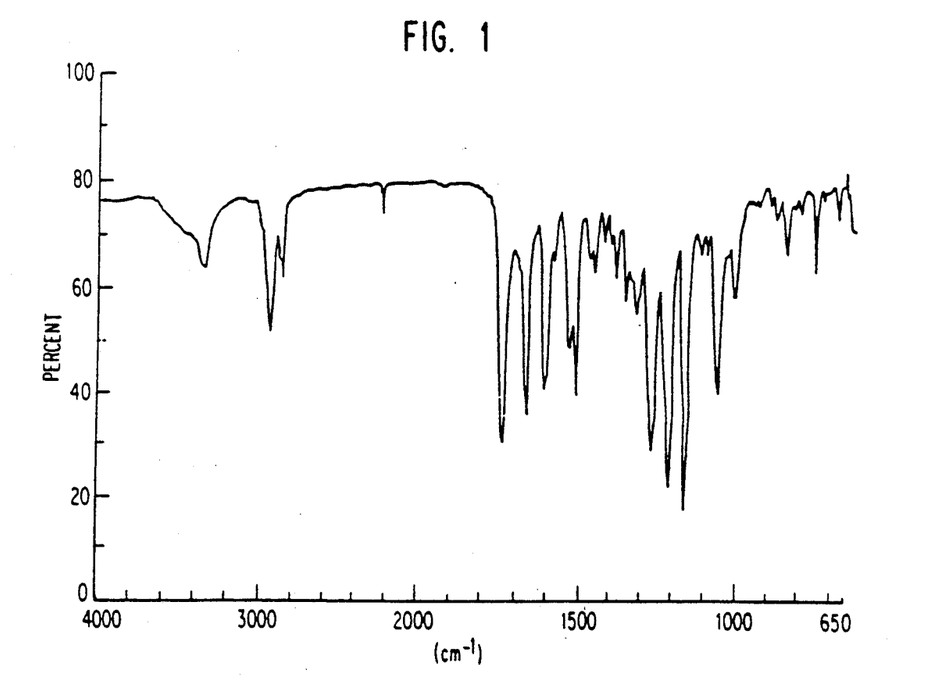
FIG. 1 is an infrared absorption spectrum of the compound of the present invention obtained in Example 1.

FIG. 1 shows the IR absorption spectrum of the product. The absorption at 2220 cm$^{-1}$ indicates the presence of —CN.

Elemental Analysis (%)

|  | C | H | N |
| --- | --- | --- | --- |
| Calculated: | 68.76 | 6.76 | 5.53 |
| Found: | 68.72 | 6.70 | 5.73 |

$^1$H-NMR [ppm]: 0.90, 1.32, 1.58, 1.85, 4.05, 4.28, 4.68, 6.87, 6.95, 7.32, 8.00, 8.12 and 8.32.

Mass spectrum [M/Z]
506:M*
461:(OC$_2$H$_5$)*
433: (M—COOC$_2$H$_5$)*
390:

291:

219:

171:

121:

EXAMPLE 2 TO 4

The procedure of Example 1 was repeated except using compounds of formula (I) wherein R, X and Y were as defined in Table 1.

The structure of each product thus obtained was confirmed by IR absorption spectrometry and 1H-NMR, similar to Example 1.

Table 1 also shows the phase transition temperatures of the products produced in Examples 1 to 4.

The mixture thus obtained was stirred at 0° C. for 2 hours and then at room temperature overnight. After distilling off the solvent, the residue was dissolved in 30 ml of ethyl acetate. The insoluble N,N'-dicyclohexyl urea was removed by filtering and the filtrate was successively washed with 30 ml of 10% citric acid, 30 ml of water, 30 ml of 4% sodium hydrogencarbonate and 30 ml of water. The organic phase was dried over magnesium sulfate and evaporated to dryness to thereby give a crude ester product.

The yield was 95%. The unpurified product was subjected to the next treatment as such.

(5-2) Synthesis of 4'-n-tetradecyloxybiphenyl-4-carboxylic acid 2.14 g of p-hydroxybiphenylcarboxylic acid and 1.12 g of potassium hydroxide were dissolved in a mixture of 300 ml of ethanol and 40 ml of water. Then 3.02 ml of tetradecyl bromide was added thereto and the mixture was heated under reflux for 12 hours. Next, 13.5 ml of 2M hydrochloric acid was added to the reaction mixture and the crystals thus precipitated were filtered. Thus 2.20 g of 4'-n-tetradecyloxybiphenyl-4-carboxylic acid was obtained.

TABLE 1

EXAMPLE 5

Synthesis of N-{4-(4'-n-tetradecyloxybiphenyl)-oxycarbonyl-α-cyanocinnamoyl}-L-isoleucine methyl ester

(5-1) Synthesis of N-(4-hydroxy-α-cyanocinnamoyl)-L-isoleucine methyl ester 1.04 g (5.5 mmole) of commercially available α-cyano-4-hydroxycinnamic acid was stirred in 10 ml of cold dichloromethane and the temperature of the reaction mixture was adjusted to 0° to 5 ° C. Then, 1.134 g (5.5 mmole) of DCC was added thereto. Approximately 20 minutes thereafter, 0.91 g (5 mmole) of commercially available L-isoleucine methyl ester hydrochloride and 0.7 ml (5 mmole) of triethylamine were added thereto.

(5-3) Synthesis of N-{4-(4'-n-tetradecyloxybiphenyl)-oxycarbonyl-α-cyanocinnamoyl}-L-isoleucine methyl ester 1.94 g of tetradecyloxybiphenylcarboxylic acid, 3.44 ml of thionyl chloride and one drop of DMF were heated under reflux for approximately 2 hours to thereby give an acid chloride. After distilling off the thionyl chloride, 1.5 g of the compound synthesized in (5-1), 1.91 ml of pyridine and 12 ml of ether were added to the residue. The obtained mixture was heated under reflux for approximately 5 hours to thereby complete esterification.

After post-treatments, the product was purified by silica gel column chromatography with the use of a mixture of n-hexane and ethyl acetate (5:1) as an eluent.

Thus 1.25 g of a crude crystalline compound was obtained. The product was further purified by recrystallization to thereby give the objective compound.

The structure of the obtained product was confirmed by infrared absorption spectrometry, elemental analysis and $^1$H-NMR as will be shown below.

Figure 2:
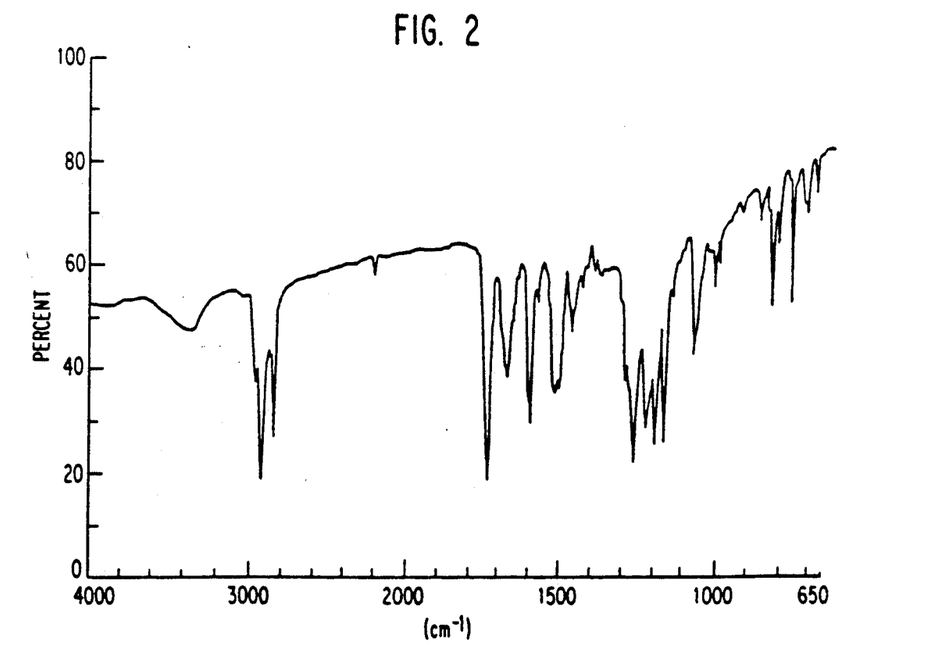
FIG. 2 is an infrared absorption spectrum of the compound of the present invention obtained in Example 5.

FIG. 2 shows the IR absorption spectrum of the product. The absorption at 2220 cm$^{-1}$ indicates the presence of —CN.

Elemental analysis (%)

|  | C | H | N |
|---|---|---|---|
| Calculated: | 74.56 | 7.96 | 3.95 |
| Found: | 74.37 | 7.81 | 3.92 |

$^1$H-NMR [ppm]: 0.91. 1.00, 1.28, 1.48, 1.83, 2.05, 3.81, 4.02, 4.71, 6.86, 7.01, 7.41, 7.62, 7.72, 8.06, 8.24 and 8.34.

Figure 3:
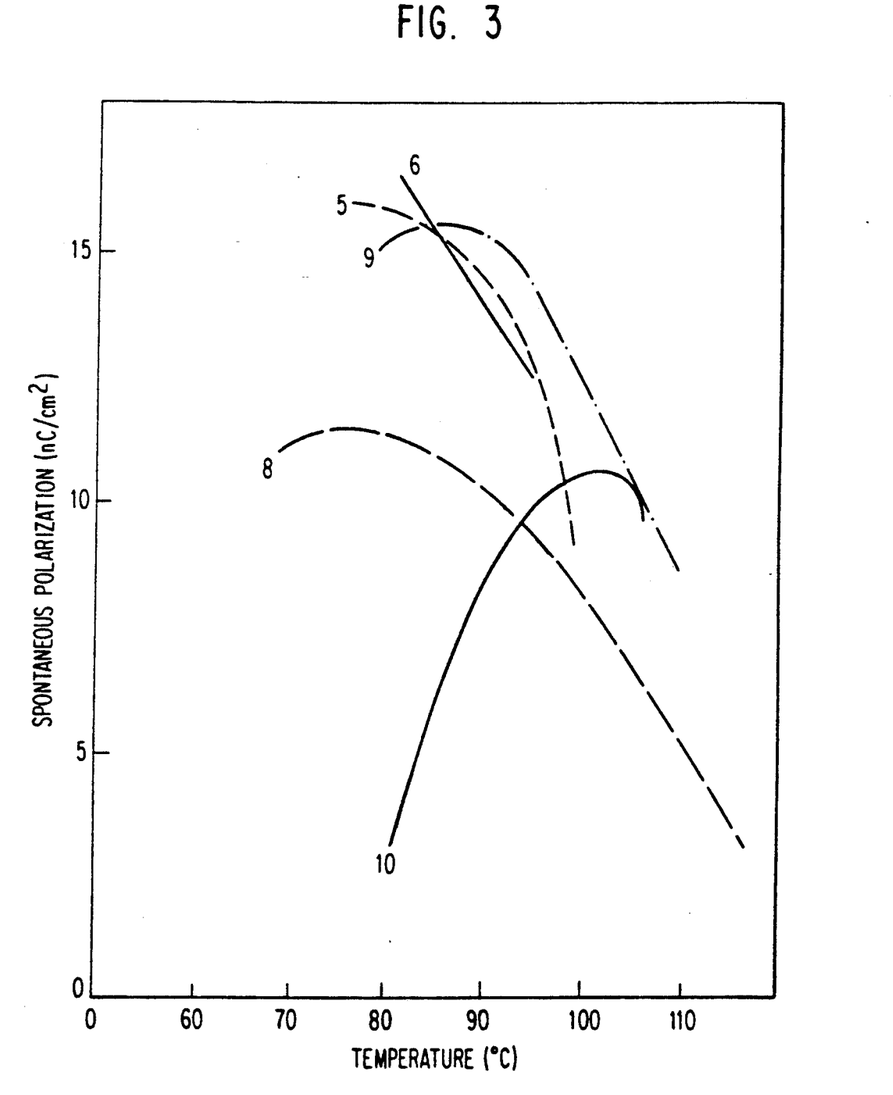
FIG. 3 shows temperature dependency of spontaneous polarization wherein the reference numerals 5, 6, 8, 9 and 10 correspond to Examples 5, 6, 8, 9 and 10 respectively.

Next, the phase transition temperature of the product was measured. Table 2 shows the result. The phase transition temperature was measured by observing the product under a polarization microscope and with the use of a differential scanning calorimeter. FIG. 3 shows the temperature dependency of spontaneous polarization.

Further, Table 2 shows the response speed. The spontaneous polarization and response speed were measured by the following methods.

Spontaneous Polarization

The compound was converted into an isotropic liquid by heating. Next, it was injected between two glass substrates provided with ITO transparent electrodes, which were located via a polyethylene terephthalate film (thickness: 3.3 μ), by the vacuum-injection method so as to give a film liquid crystal cell. Then, the obtained cell was slowly cooled under temperature gradient in accordance with the spacer-edge method as described in Ishikawa et al., *Japanese Journal of Applied Physics*, vol. 23, No. 4, p. L211, (1984). Thus the $S_A$ phase was aligned. Further, the temperature was lowered to the $S_A$–$S_C*$ phase transition temperature.

Then the spontaneous polarization was determined by the triangle wave voltage application method as described in Miyasato et al., *Japanese Journal of Applied Physics*, vol. 22, No. 10, p. L661, (1983), while further lowering the temperature (applied voltage: 30 $V_{p-p}$, 50 Hz). Thus, the spontaneous polarization changed with the temperature as shown by curve 5 in FIG. 3.

Response Speed

Rectangular wave voltage (40-50 $V_{p-p}$, 200-1000 Hz) was applied to the same film liquid crystal cell as the one described above at a temperature lower than the $S_A$–$S_C*$ phase transition temperature. Then, the cell was irradiated with He-Ne laser (632.8 nm) under a polarization microscope (under crossed Nicol's prisms). The time period required for increasing the amount of the transmitted light from 10% to 90% (or decreasing the same from 90% to 10%) was measured. Table 2 shows the results.

EXAMPLES 6 TO 14

The procedure of Example 5 was repeated except by using compounds of formula (I) wherein R, X, Y and Z were as defined in Table 2.

The structure of each product thus obtained was confirmed by IR absorption spectrometry and $^1$H-NMR, similar to Example 5. The phase transition temperature, temperature dependency of spontaneous polarization and response speed of each product thus obtained were examined by the same methods as those employed in Example 5. Table 2 shows the phase transition temperatures and response speeds of the products of Examples 6 to 14.

FIG. 3 shows the temperature dependency of spontaneous polarization.

These results indicate that the amino acid derivatives of the present invention show smectic phases over a wide and relatively low temperature range of from 20° to 179° C. Among these smectic phases, a chiral smectic C phase ($S_C*$ phase), which show ferroelectric and is particularly useful, showing spontaneous polarization at a lower temperature is the more advantageous.

When formulated into a liquid crystal device, the amino acid derivative of the present invention showing an $S_C*$ phase shows a response speed of 44 to 120 μsec., which is approximately 1/10 times as short as those of known ones.

TABLE 2

| Example No. | R | X | Y | Z | Phase Transition Temperature (°C.) | Response Speed (μsec) |
|---|---|---|---|---|---|---|
| 5 | —C$_{14}$H$_{29}$ | —CH$_3$ | —CH(CH$_3$)CH$_2$CH$_3$ | —CN | Cry $\underset{45}{\overset{63}{\rightleftarrows}}$ S$_X*$ $\underset{76}{\overset{}{\rightleftarrows}}$ S$_C*$ $\underset{104}{\overset{107}{\rightleftarrows}}$ S$_A$ $\underset{120}{\overset{125}{\rightleftarrows}}$ Iso | 80 |
| 6 | —C$_{12}$H$_{25}$ | —CH$_3$ | " | " | Cry $\underset{50}{\rightleftarrows}$ S$_X*$ $\underset{107}{\overset{90}{\rightleftarrows}}$ S$_C*$ $\underset{109}{\overset{106}{\rightleftarrows}}$ S$_A$ $\underset{135}{\overset{132}{\rightleftarrows}}$ Iso | 104 |
| 7 | —C$_7$H$_{15}$ | —CH$_3$ | " | " | Cry $\underset{40}{\rightleftarrows}$ S$_X*$ $\underset{92}{\overset{100}{\rightleftarrows}}$ S$_A$ $\underset{100}{\overset{100}{\rightleftarrows}}$ Iso | |
| 8 | —C$_{14}$H$_{29}$ | —C$_2$H$_5$ | —CH(CH$_3$)$_2$ | " | Cry $\underset{62}{\overset{79}{\rightleftarrows}}$ S$_X*$ $\underset{88}{\overset{105}{\rightleftarrows}}$ S$_C*$ $\underset{114}{\rightleftarrows}$ S$_A$ $\underset{139}{\overset{140}{\rightleftarrows}}$ Iso | 120 |
| 9 | —C$_{14}$H$_{29}$ | —CH$_3$ | " | " | Cry $\underset{54}{\overset{88}{\rightleftarrows}}$ S$_X*$ $\underset{117}{\overset{120}{\rightleftarrows}}$ S$_C*$ $\underset{124}{\overset{125}{\rightleftarrows}}$ S$_A$ $\underset{147}{\overset{154}{\rightleftarrows}}$ Iso | 55 |
| 10 | —C$_{12}$H$_{25}$ | —CH$_3$ | " | " | Cry $\underset{44}{\overset{58}{\rightleftarrows}}$ S$_X*$ $\underset{115}{\overset{119}{\rightleftarrows}}$ S$_C*$ $\underset{122}{\overset{125}{\rightleftarrows}}$ S$_A$ $\underset{146}{\overset{148}{\rightleftarrows}}$ Iso | 44 |

TABLE 2-continued

| Example No. | R | X | Y | Z | Phase Transition Temperature (°C.) | Response Speed (μsec) |
|---|---|---|---|---|---|---|
| 11 | —C$_7$H$_{15}$ | —CH$_3$ | " | " | Cry $\underset{61}{\overset{170}{\rightleftarrows}}$ S$_X$* $\underset{106}{\rightleftarrows}$ S$_A$ $\underset{169}{\rightleftarrows}$ Iso | |
| 12 | —C$_{12}$H$_{25}$ | —C$_2$H$_5$ | —CH$_2$CH(CH$_3$)$_2$ | " | Cry $\underset{20}{\overset{62}{\rightleftarrows}}$ S$_X$* $\underset{93}{\overset{96}{\rightleftarrows}}$ S$_A$ $\underset{121}{\overset{122}{\rightleftarrows}}$ Iso | |
| 13 | —C$_{12}$H$_{25}$ | —C$_2$H$_5$ | —CH$_3$ | " | Cry $\underset{105}{\rightleftarrows}$ S$_X$* $\underset{146}{\overset{149}{\rightleftarrows}}$ S$_A$ $\underset{176}{\overset{179}{\rightleftarrows}}$ Ch $\underset{179}{\overset{181}{\rightleftarrows}}$ Iso | |
| 14 | —C$_{12}$H$_{25}$ | —CH$_3$ | —CH(CH$_3$)$_2$ | —CH$_3$ | Cry $\underset{101.0}{\overset{117.6}{\rightleftarrows}}$ S$_X$* $\underset{114.3}{\rightleftarrows}$ S$_A$ $\underset{136.5}{\overset{137.0}{\rightleftarrows}}$ Iso | |

Now, examples of known liquid crystals having an amino acid in the structure will be shown for comparison.

COMPARATIVE EXAMPLE 1

Using the compound having the following structure as described in JP-A-62-89648, the same procedure as in Example 5 were repeated.

CH$_3$(CH$_2$)$_7$OC$_6$H$_4$C$_6$H$_4$COOC$_6$H$_4$CONHC*HCOO—CH$_2$CH$_3$
                                         |
                                         CH$_3$

The phase transition temperature was as follows: Cry-S$_A$ 176.8° C.; S$_A$-I$_{SO}$ 179.1° C.; S$_A$-S$_C$ 154.7° C.

The liquid crystal showed a smectic phase at 176° C. which is much higher temperature than those of the liquid crystals of the present invention.

COMPARATIVE EXAMPLE 2

The compound of formula (I) wherein R, X, Y and Z are —C$_7$H$_{15}$, —C$_2$H$_5$, —CH$_2$CH$_2$SCH$_3$ and —CN, respectively, was prepared.

Although methionine was introduced thereto as an optically active amino acid, the compound showed no phase transition at the melting point of 83.6° C.

It is seen from Examples 1 to 4 that, the compounds of the present invention show cholesteric phases over extremely wide temperature ranges around room temperature. It is also seen from Examples 5 to 14 that, the compounds of the present invention, which are produced by using relatively inexpensive amino acids as materials for optically active moieties, show smectic phases, in particular, useful S$_C$* phase over a wide temperature ranges around room temperature. Therefore, the present invention provides a novel, useful and inexpensive compound which may be used, either alone or in the form of a mixture with other nematic, smectic or ferroelectric liquid crystals, as a material for a liquid crystal display device showing an electrooptical effect over a practically useful temperature range.

While the invention has been described in detail and with reference to specific embodiments thereof, it will be apparent to one skilled in the art that various changes and modifications can be made therein without departing from the spirit and scope thereof.

What is claimed is:

1. An optically active amino acid derivative represented by formula (I):

R—O—A—COO——CH=C—CONH—C*H—COOX
                                    |                    |
                                    Z                    Y wherein R represents a straight chain alkyl group having 6 to 16 carbon atoms; A represents X represents a straight chain alkyl group having 1 to 14 carbon atoms; Y represents —CH$_3$, —CH$_2$CH(CH$_3$)$_2$, —CH(CH$_3$)$_2$, —CH(CH$_3$)CH$_2$CH$_3$ or and Z represents —CH$_3$ or a hydrogen atom.

2. An optically active amino acid derivative as in claim 1, wherein R represents a straight chain alkyl group having 7 to 14 carbon atoms, X represents a straight chain alkyl group having 1 to 3 carbon atoms, and Y represents —CH(CH$_3$)$_2$ or —CH(CH$_3$)CH$_2$CH$_3$.

* * * * *